(12) United States Patent
Ramsden et al.

(10) Patent No.: US 7,876,447 B2
(45) Date of Patent: Jan. 25, 2011

(54) MONOFIBRE OPTICAL METER FOR CHEMICAL MEASUREMENT

(75) Inventors: Jeremy Joachim Ramsden, Ampthill (GB); Yosyp Petrovich Sharkan, Uzhgorod (UA); Serhiy Korposh, Kitakyushu (JP); Mikhaylo Yurievich Sichka, Uzhgorod (UA); Nikolay Borisovich Zhitov, Moscow (RU)

(73) Assignee: Cranfield University, Granfield (GB)

( * ) Notice: Subject to any disclaimer, the term of this patent is extended or adjusted under 35 U.S.C. 154(b) by 309 days.

(21) Appl. No.: 12/018,693

(22) Filed: Jan. 23, 2008

(65) Prior Publication Data

US 2009/0185169 A1 Jul. 23, 2009

(51) Int. Cl.
*G01B 9/02* (2006.01)
(52) U.S. Cl. ...................................... 356/480
(58) Field of Classification Search ................ 356/454, 356/477, 480; 385/12
See application file for complete search history.

(56) References Cited

U.S. PATENT DOCUMENTS

| | | | |
|---|---|---|---|
| 4,430,565 A * | 2/1984 | Brogardh et al. | 250/227.23 |
| 4,778,987 A * | 10/1988 | Saaski et al. | 250/226 |
| 5,337,376 A * | 8/1994 | Ravetti et al. | 385/12 |
| 5,804,453 A | 9/1998 | Chen | |
| 5,864,641 A * | 1/1999 | Murphy et al. | 385/12 |
| 6,141,098 A | 10/2000 | Sawatar et al. | |

FOREIGN PATENT DOCUMENTS

| | | |
|---|---|---|
| GB | 2096784 A | 10/1982 |
| GB | 2385915 A | 9/2003 |
| WO | 01/36945 A1 | 5/2001 |
| WO | 2006/074444 A2 | 7/2006 |

* cited by examiner

*Primary Examiner*—Michael A Lyons
(74) *Attorney, Agent, or Firm*—Polster, Lieder, Woodruff & Lucchesi, L.C.

(57) ABSTRACT

Apparatus for determining a parameter of a sample has an optical sensor in the form of a monofibre waveguide having a distal end coated with a film that is placed in a sample. The waveguide has an input channel connected to a radiation light source and an output channel connected to a photodiode and amplifier to receive signals representative of the interference patterns created at the interface between the film and the sample. A computer receives the signals via an analogue to digital converter for processing the information and providing a measurement of the parameter. The measurement of the parameter may be used to control a process or system.

24 Claims, 3 Drawing Sheets

MONOFIBRE OPTICAL METER FOR CHEMICAL MEASUREMENT

CROSS-REFERENCE TO RELATED APPLICATIONS

Not Applicable.

STATEMENT REGARDING FEDERALLY SPONSORED RESEARCH

Not Applicable.

BACKGROUND OF THE INVENTION

The present invention is related generally to a method and apparatus for detecting chemical changes in a solution, and in particular, to a method and apparatus for employing optical sensors to measure changes in optical interference patterns resulting from chemical changes in a solution.

The concept of using changed in the optical properties of a fibre optic sensor to detect chemical changes in solution has been described in the present art.

However, the method of detection in these cases has been to monitor the absorbance or fluorescence of a surface coating on the sensor tip.

The present invention utilizes the measurement of changes in interference patterns of layers deposited on the sensor tip. The main advantages of this method include increased sensitivity compared with absorbance and fluorescence changes; increased robustness and universality, i.e., the same sensing platform can be used to cover a very wide range of analytes.

BRIEF SUMMARY OF THE INVENTION

Briefly stated, the present disclosure provides an apparatus for determining a parameter of a sample utilizing an optical sensor in the form of a monofibre waveguide having a distal end coated with a film that is placed in a sample. The waveguide has an input channel connected to a radiation light source and an output channel connected to a photodiode and amplifier to receive signals representative of the interference patterns created at the interface between the film and the sample. A computer receives the signals via an analogue to digital converter for processing the information and providing a measurement of the parameter. The measurement of the parameter may be used to control a process or system.

The foregoing features, and advantages set forth in the present disclosure as well as presently preferred embodiments will become more apparent from the reading of the following description in connection with the accompanying drawings.

BRIEF DESCRIPTION OF THE SEVERAL VIEWS OF THE DRAWINGS

In the accompanying drawings which form part of the specification.

Corresponding reference numerals indicate corresponding parts throughout the several figures of the drawings. It is to be understood that the drawings are for illustrating the concepts set forth in the present disclosure and are not to scale.

Figure 1:
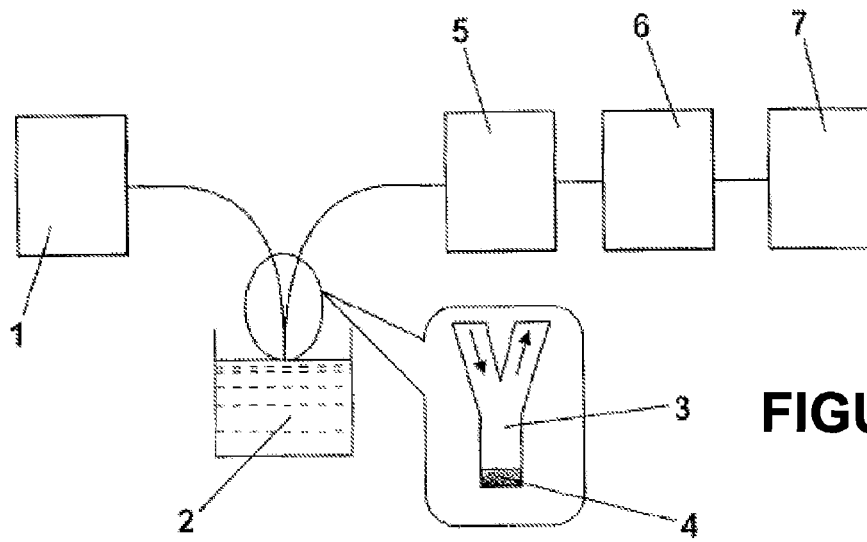
FIG. 1 is a simplified block diagram representing a monofibre optical pH probe of the present invention.

Before any embodiments of the invention are explained in detail, it is to be understood that the invention is not limited in its application to the details of construction and the arrangement of components set forth in the following description or illustrated in the drawings.

DETAILED DESCRIPTION

The following detailed description illustrates the invention by way of example and not by way of limitation. The description enables one skilled in the art to make and use the present disclosure, and describes several embodiments, adaptations, variations, alternatives, and uses of the present disclosure, including what is presently believed to be the best mode of carrying out the present disclosure.

The present invention is directed to fibre-optic sensors, or a module made up of a plurality of such sensor devices, having a reactive film or films deposited on their end surfaces. The invention is a fibre-optic sensor utilizing a refractive film producing an interference system, as shown in FIG. 1. In the figure, a radiation source (1) is shown coupled to a Y-shaped monofibre (3) having a thin-film coating (4) on an end thereof. The coated end (4) of the monofibre (3) is placed within a sample (2), with opposite branches of the monofibre (3) coupled to the radiation source (1) for receiving incoming radiation, and a photodiode (5) for receiving returned radiation. The output of the photodiode (5) is amplified and passed to an analog-to-digital converter (6) for subsequent processing by a computer system (7).

The invention possesses an optically refractive layer or series of optically refractive layers that are designed to produce a predictable interference pattern due to the combination of reflections at the interface between the fibre and the layer, and at the interface between the layer and the ambient medium.

In conventional fibre-optic sensor devices there is a use of a thin film, whose color, absorbance or fluorescence changes according to the chemical composition of the sample to be measured, without producing an interference pattern.

Figure 2:
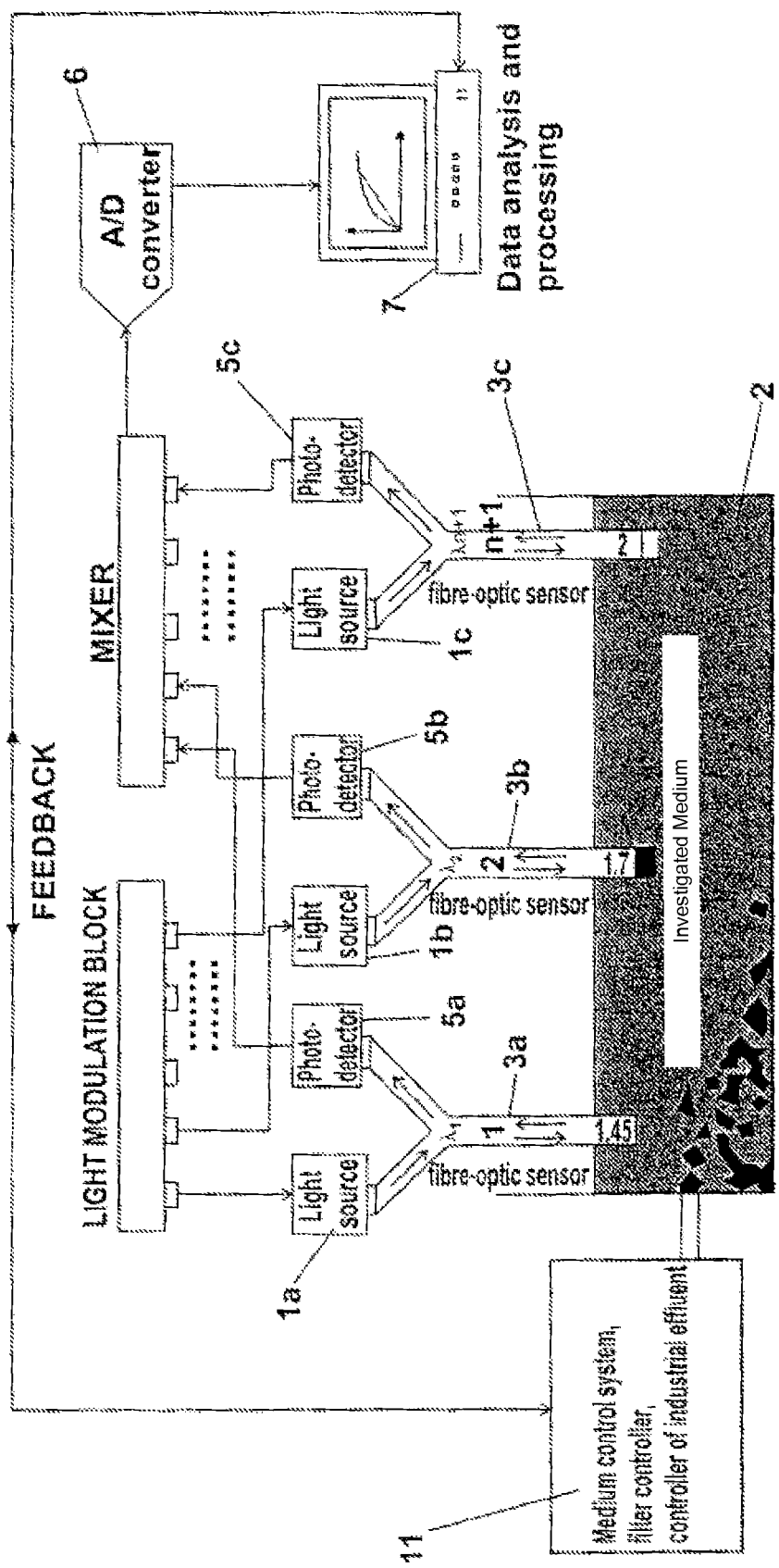
FIG. 2 is a schematic of a complete sensing system of the present invention.

The basis of the sensor operation is the recordation of the signal phase change taking place as a result of the changed of the reactive film thickness $d_2$ and/or the reactive film refractive index (r.i.) $n_2$ due to the interaction of the film with the sample. In a simpler but less informative realization, the amplitude alone of the output channel can be measured as an indication of changed in the sensor film As shown in FIG. 2, these sensors may be very conveniently incorporated into a complete sensing system. As shown in FIG. 2, a medium (2) undergoing investigation is regulated by a medium control system (11), which may be a filter controller or other controller of an industrial effluent. A radiation controller (light modulation block) is coupled to a plurality of light sources (1a, 1b, 1c) which in turn are linked through Y-shaped fibre optic sensors having end-film coatings, to the medium (2) under investigation, and to a plurality of associated photodiodes or photo detectors (5a, 5b, 5c). Output from the photo detectors (5a, 5b, and 5c) is routed through a mixer (multiplexer), to an analog to digital converter (6), for subsequent communication to a data analysis and processing system (7).

With the film on the sensor ends, multiray interference takes place according to the formula:

$$n_2 d_2 = \frac{m\lambda}{4} \qquad \text{Eqn. 1}$$

where $\lambda$ represents the wavelength of the radiation in the optical fibre, and m represents the number of interference maximum observed in the film.

The output voltage V of the detector depends linearly on the reflection coefficient R, defined as:

$$R = \kappa V \qquad \text{Eqn. 2}$$

Figure 3:
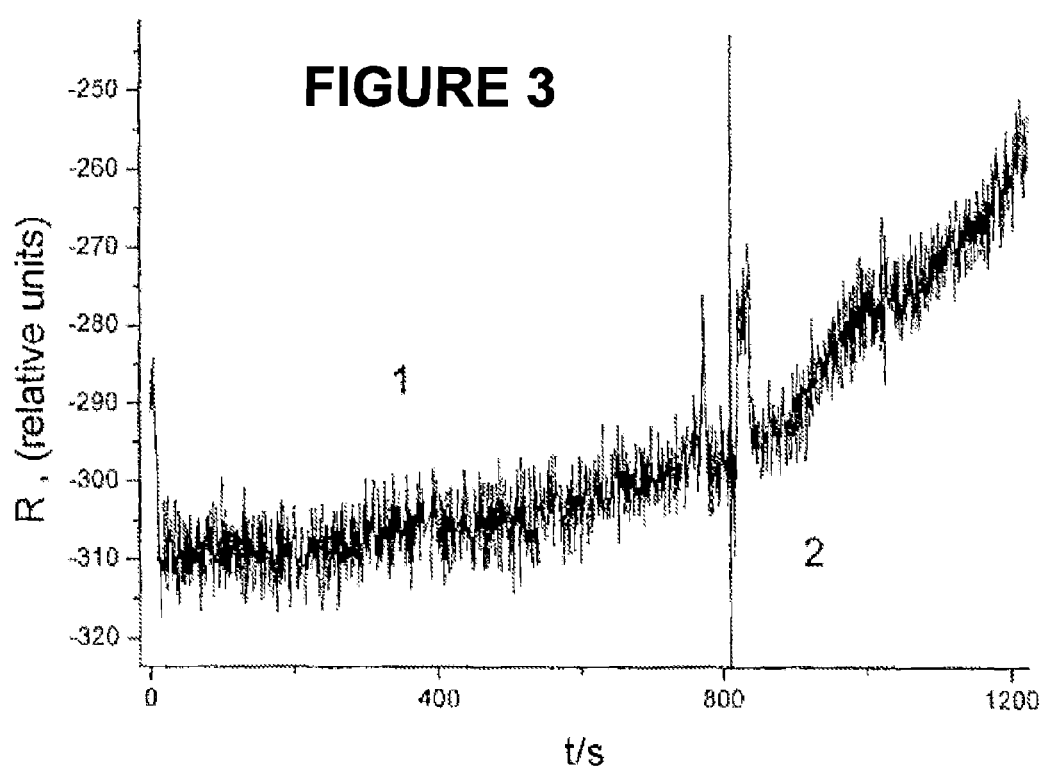
FIG. 3 graphically illustrates changes in reflection when an optical fibre probe having a $Ge_{33}As_{12}Se_{55}$ film is place into two samples of different concentrations of sodium hydroxide solution.

In order to determine the proportionality constant $\kappa$, i.e. to calibrate the device, the response from a medium of known r.i. needs to be measured. The reflection coefficient is given by:

$$R = \left(\frac{n_1 - n_3}{n_1 + n_3}\right)^2 \qquad \text{Eqn. 3}$$

where $n_1$ and $n_3$ are the refractive indices of the quartz monofibre and the medium surrounding its end, respectively. If $n_1$ is unknown, then the response from two media of known r.i. need to be measured and the corresponding two Eqns. 3 solved to find $n_1$. FIG. 3 illustrates a typical example of the changed in reflection occurring when a fibre is plunged from air ($n_3 \approx 1.00$) into water ($n_3 \approx 1.33$) (at t≈10 s) and then withdrawn (at t≈60 s).

In order to select a material for sensitizing the fibre end, i.e. that interacts optimally with the sample (experimental medium), a number of requirements have to be met:

First, the film should dissolve in the experimental medium via progressive thinning down. Destruction of the film via fragmentation and release of particles at least as big as the wavelength of the radiation used is to be avoided. Alternatively, the film should swell or contract with penetration of selected components of the experimental medium. A further possibility is for selected components of the sample to form layerwise deposits on the film coating the fibre end.

Second, the rate of dissolution or swelling, or their converses, deposition or contraction, should be convenient for the method of recording used.

Third, the material must be optically transparent to the radiation used.

Fourth, there must be a practicable method for depositing the film on the ends of the optical fibres.

The performance of interference systems can be predicted by modeling the optical arrangement as a multilayer interference system in which the fibre is a transparent substrate and the film is an optically transparent layer deposited on the substrate. The coefficient of reflection $R_{123}$ for such a system is, taking account of the multiray interference of light beams reflected from the two boundaries of the deposited film (considered as a homogeneous medium located between two homogeneous layers, in general different media) is expressed in Eqn. 4 as:

$$R_{123} = \frac{(n_3^2 + n_2^2)(n_2^2 + n_1^2) - 4n_3 n_2^2 n_1 + (n_3^2 - n_2^2)(n_2^2 - n_1^2)\cos 2\beta}{(n_3^2 + n_2^2)(n_2^2 + n_1^2) + 4n_3 n_2^2 n_1 + (n_3^2 - n_2^2)(n_2^2 - n_1^2)\cos 2\beta}$$

where n1 is the index of refraction of the quartz monofibre, n2 is the index of refraction of the film, n3 is the refraction coefficient of the medium under investigation, and $$\beta = \frac{2\pi}{\lambda} n_2 d_2 \qquad \text{Eqn. 5}$$

From Eqn. (4), it is clear that the sensitivity of the response towards different concentrations of analyte (investigated medium) subtly depend on the material properties of the system, especially the indices of refraction.

In practice it is very important, especially in current medical-biological investigations, to determine the dynamics of change of the concentrations of the experimental solutions under investigation. Equation (4) also shows how the rate of change of $R_{123}$, $dR_{123}/dt$, will depend on the rate of etching, $dd_2/dt$, which in turn depends on the rate of analyte concentration, and the time dependences of the concentrations can also be conveniently determined by following the time dependence of the differential coefficients.

Returning generally to FIG. 1, the sensor comprises a Y-type distributor (3) that divides the power equally between the input and output channels. From the input channel the signal propagates into the common channel, which is placed in contact with the sample (2). The optical signal is reflected from the interface with the sample (2) and returns to the common channel. The signal propagates from the common channel into the output channel from which the signal is received and amplified (5), converted (6), and processed (7). The device is as described in FIG. 1, where a radiation source (1) may be, but is not limited to, a light-emitting diode (1) (emitting a wavelength of 0.95 μm in the present work; any wavelength in ultraviolet, visible, or infrared spectral regions is suitable), connected to a Y-shaped monofibre (3) that is coated with a thin film deposit (4). The coated tip is placed in the sample (2) and the reflected light is passed to a photodiode and amplifier (5), and then to an analog-to-digital converter (ADC) (6). The signals from the ADC (6) are then passed to a computer (7) for information processing and readout.

In a general embodiment, the invention can be used to analyze the composition of any solution, provided that the optical waveguide or waveguides are coated with an appropriate material. In these embodiments the coating or coatings would selectively and predictably change, e.g. be degraded by active chemical processes, in the presence of the analyte whose concentration it is wished to measure. An example of an active degradation process would be in the action of enzymes on the film causing a reduction in thickness of the film. In other embodiments the coating may dissolve in the presence of the analyte, for example in a pH analyzer the coating may dissolve in the presence of $OH^-$ ions. The coating may also increase in thickness in the presence of an analyte which in some embodiments may be polymers that selectively swell in the presence of one or more analytes. In yet other embodiments the coating may be a material with the capacity to absorb the analyte, hence changing the refractive index of the coating. In all these embodiments, the principle is that one or more interactions between the analyte and the coating change the optical thickness of the coating, and the concentration of analyte affects either the instantaneous magnitude of the change or the rate of change.

In an embodiment where there are multiple coated sensors, probes can be assembled from bundles of fibres, each coated with a different sensitive film, allowing the measurement of many analytes simultaneously as shown in FIG. 2. Such bundles can include uncoated reference fibred to allow the measured responses of the measurement fibres to be compensated for bulk refractive index changes of the medium under investigation. Hence as well as functioning as a chemical or biochemical sensor, the device can also function as a physical sensor to measure parameters such as temperature.

In a particular embodiment the invention is a novel film-coated fibre-optic probe which is capable of continuously determining the pH of solutions by using the amplitude of the interference pattern generated when the probe is immersed in the solution to be investigated. Continuous control of changes in the solutions is also possible. Selectivity of response is achievable by the choice of material for coating the fibre end. In the examples (chalcogenide glasses) presented here, the rate of dissolution of the chalcogenide film in alkaline media depends on the chemical composition of the film and the chemical composition (pH) of the medium under study.

In the embodiment of a pH analyzer suitable coating materials are the chalcogenide semiconductor glasses (from the Ge—As—Ge and As—Se—As systems): they are soluble in alkaline media (pH>7), transparent in the near infrared spectrum region and are easily deposited as films. The films of chalcogenide glass are deposited onto the surface of the common channel to a thickness of 3-5 µm.

For use in acid media (pH<7) films of oxide glasses are used, which dissolve even at very low concentrations of the acid substance.

In these particular embodiments bulk glasses are vacuum evaporated onto the surface of many monofibres simultaneously. This serves to produce uniform optical properties, necessary for reproducible mass production of devices.

In general, the reactive film may be deposited on the sensor tip by techniques of physical vapor deposition (reactive and nonreactive sputtering, evaporation, plasma spray), chemical vapor deposition, sol-gel or other methods known in the art.

Turning to FIG. 3, a first example shows a typical response of a $Ge_{33}As_{12}Se_{55}$ film deposited on the fibre end to two NaOH solutions (0.1% [1] and 1.0% [2]) of different concentrations. The sudden fluctuation at the boundary between the two solutions are an artifact of transferring the sensor from one solution to the other. Over these short intervals, the change in the interference pattern is almost linear. The monotonous increase of the reflectance with time as etching proceeds is due to the decrease of film thickness, which shifts the interference pattern. When the NaOH concentration is increased tenfold the slope of the reflectance versus time curve increases markedly (region [2] in FIG. 3). The slopes of short intervals—and mV/s bearing in mind that the actual numerical values are the voltages output by the photo detector (5 in FIG. 1)—correspond to pH values of 12.4 and 13.4 respectively. This type of film is useful for rather alkaline solutions.

Figure 4:
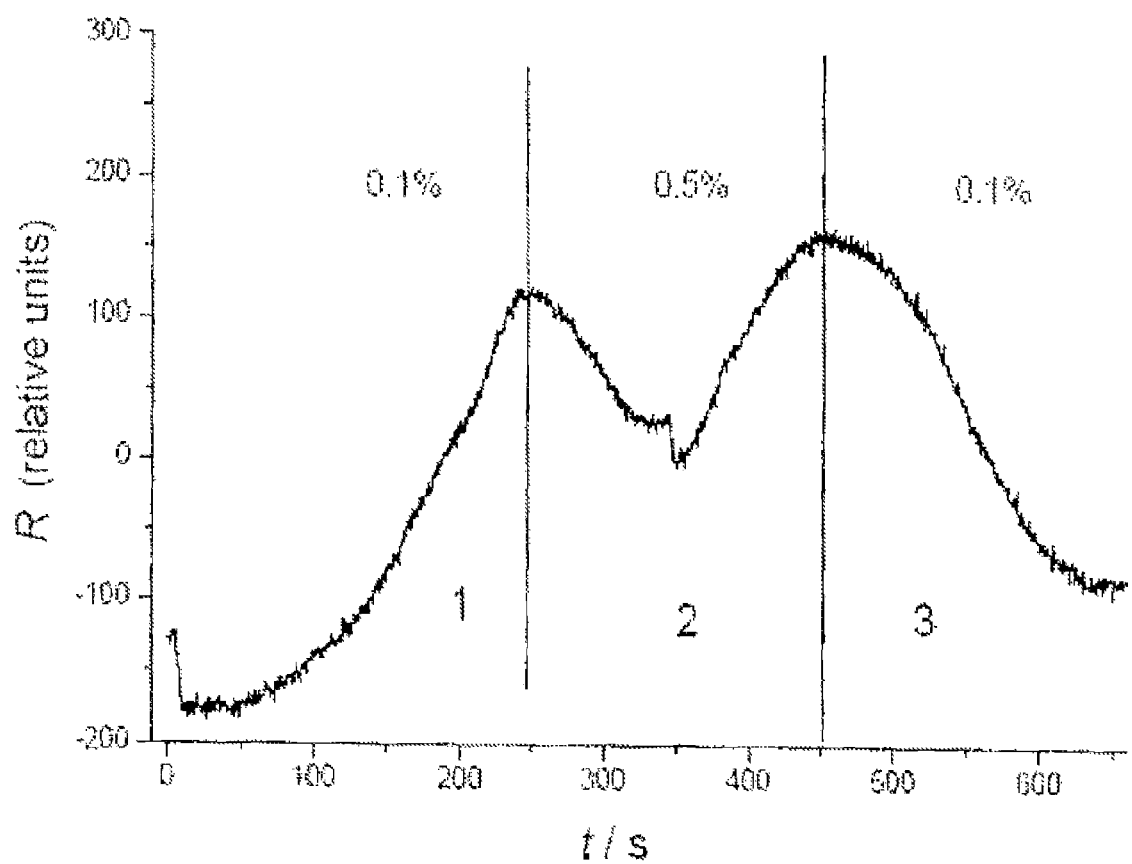
FIG. 4 graphically illustrates changes in reflection when an optical fibre probe having a $As_2Se_3$ film is place into samples of different concentrations of sodium hydroxide solution.

Turning to FIG. 4, a second example shows a typical response of a $As_2Se_3$ film deposited on the fibre end to NaOH solutions. Unlike the glass containing Ge (Example 1), $As_2Se_3$ glass is known to interact with alkali without disintegrating, and hence a smoothly continuous thinning down of the film is expected. Experimental results confirm this expectation, i.e. the noise amplitude is much lower than in FIG. 3, in which disintegration is taking place and the predicted sinusoidal interference pattern (cf. Eqn. 4) is now observed, in contrast to FIG. 3. The rate of the phase change for the given etching process, and correspondingly the change of the interference pattern, greatly depends on the alkali solution concentration. In FIG. 4 it can be seen that at a small alkali concentration (region 1) the rate of the phase change is several times smaller than at the larger concentration (region 2, compared especially to the second half with the change in region 1). The reversibility of the response was verified by adding distilled water to the medium (region 3), and a reversion to the kinetics characteristic of region 1 was noted. It may be advantageous to mechanically mix the solution.

The present disclosure can be embodied in-part in the form of computer-implemented processes and apparatuses for practicing those processes. The present disclosure can also be embodied in-part in the form of computer program code containing instructions embodied in tangible media, such as floppy diskettes, CD-ROMs, hard drives, or an other computer readable storage medium, wherein, when the computer program code is loaded into, and executed by, an electronic device such as a computer, micro-processor or logic circuit, the device becomes an apparatus for practicing the present disclosure.

The present disclosure can also be embodied in-part in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the present disclosure. When implemented in a general-purpose microprocessor, the computer program code segments configure the microprocessor to create specific logic circuits.

As various changes could be made in the above constructions without departing from the scope of the disclosure, it is intended that all matter contained in the above description or shown in the accompanying drawings shall be interpreted as illustrative and not in a limiting sense.

The invention claimed is:

1. Apparatus for determining a parameter of a sample, the apparatus comprising a plurality of sensors each comprising a monofibre waveguide having a distal end that, in use, is placed in contact with a sample, said plurality of sensors including at least one reference sensor and at least one optical sensor, said optical sensor having a reactive film at the distal end thereof such that, in use, an interference pattern representative of a parameter of the sample is produced due to reflections at an interface between the monofibre wave guide and the reactive film and an interface between the reactive film and the sample.

2. Apparatus according to claim 1 wherein the reactive film comprises one or more optically refractive layers configured to produce a predictable interference pattern.

3. Apparatus according to claim 1 wherein the reactive film is deposited on an end surface of the monofibre wave guide.

4. Apparatus according to claim 3 wherein the monofibre and reactive film are transparent.

5. Apparatus according to claim 1 wherein the thickness of the reactive film changes in the presence of the sample.

6. Apparatus according to claim 5 wherein the film dissolves to produce a reduction in thickness of the film.

7. Apparatus according to claim 5 wherein the film swells or contracts to produce an increase or reduction in thickness of the film.

8. Apparatus according to claim 5 wherein an increase in thickness of the film is produced by deposition from the sample.

9. Apparatus according to claim 1 comprising a Y-type distributor having an input channel, an output channel and a common channel.

10. Apparatus according to claim 9 wherein the input channel provides an input signal to the common channel that is reflected from the interface with the sample and provides an output signal via the common channel to the output channel.

11. Apparatus according to claim 10 wherein the input signal is provided by a radiation source.

12. Apparatus according to claim 11 wherein the radiation source is an LED light source.

13. Apparatus according to claim 10 wherein the output signal is provided to a radiation detector.

14. Apparatus according to claim 13 wherein the radiation detector is a photodiode.

15. Apparatus according to claim 13 wherein the radiation detector Is further configured to provide an output to a computer via an amplifier and an analogue-digital converter (ADC), the computer being operable to process information from the radiation detector and provide a measurement of the parameter of the sample.

16. Apparatus according to claim 1 wherein each optical sensor has a different sensitivity.

17. Apparatus according to claim 1 wherein the apparatus functions as a chemical or biochemical sensor.

18. Apparatus according to claim 17 wherein the apparatus functions as a pH sensor.

19. Apparatus according to claim 1 wherein the apparatus functions as a physical sensor.

20. Apparatus according to claim 19 wherein the apparatus functions as a temperature sensor.

21. Apparatus according to claim 1 wherein the refractive index of the reactive film changes in the presence of the sample.

22. Apparatus according to claim 1 wherein the at least one reference sensor is uncoated.

23. Apparatus according to claim 1 wherein a measured response of the at least one optical sensor to bulk refractive index changes of the sample is compensated by the at least one reference sensor.

24. A method of determining a parameter of a sample comprising providing a plurality of sensors each comprising a monofibre wavequide having a distal end, said plurality of sensors including at least one reference sensor and at least one optical sensor, providing said at least one optical sensor with a reactive film at the distal end thereof, placing the distal end of the sensors in contact with a sample, providing a radiation source and producing an interference pattern due to reflections at an interface between the monofibre waveguide and the reactive film and at an interface between the reactive film and the sample with the radiation source, and using the interference pattern to determine a parameter of the sample.

* * * * *